United States Patent
Shoji et al.

(10) Patent No.: US 8,623,084 B2
(45) Date of Patent: Jan. 7, 2014

(54) SOFT INTRAOCULAR LENS

(75) Inventors: Noriyuki Shoji, Kitamoto (JP); Masanobu Inoue, Honjo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 12/997,969

(22) PCT Filed: Jun. 19, 2008

(86) PCT No.: PCT/JP2008/061212
§ 371 (c)(1),
(2), (4) Date: Dec. 24, 2010

(87) PCT Pub. No.: WO2009/153873
PCT Pub. Date: Dec. 23, 2009

(65) Prior Publication Data
US 2011/0130832 A1 Jun. 2, 2011

(51) Int. Cl.
*A61F 2/16* (2006.01)
(52) U.S. Cl.
USPC .......................................... 623/6.46
(58) Field of Classification Search
USPC ............ 623/6.11, 6.18, 6.38–6.43, 6.46, 6.21
See application file for complete search history.

(56) References Cited

U.S. PATENT DOCUMENTS

| | | | | |
|---|---|---|---|---|
| 5,716,403 | A * | 2/1998 | Tran et al. ..................... | 623/6.46 |
| 6,179,870 | B1 | 1/2001 | Sourdille | |
| 2007/0260308 | A1 | 11/2007 | Tran | |
| 2009/0043384 | A1 | 2/2009 | Niwa | |

FOREIGN PATENT DOCUMENTS

| | | |
|---|---|---|
| EP | 1882461 A1 | 1/2008 |
| EP | 1882462 A1 | 1/2008 |
| JP | 63-240856 A | 10/1988 |
| JP | 06-233786 A | 8/1994 |
| JP | 10-513099 A | 12/1998 |
| JP | 2000-509615 A | 8/2000 |
| JP | 2007-089810 A | 4/2007 |
| JP | 2007-296356 A | 11/2007 |
| WO | WO 97/20523 A1 | 6/1997 |
| WO | WO 97/41805 A1 | 11/1997 |
| WO | WO 2006/123427 A1 | 11/2006 |
| WO | WO 2006/123428 A1 | 11/2006 |

OTHER PUBLICATIONS

PCT International Search Report dated Jul. 4, 2008 for PCT App. Ser. No. PCT/JP08/61212.

* cited by examiner

*Primary Examiner* — William H. Matthews
(74) *Attorney, Agent, or Firm* — Henricks, Slavin & Holmes LLP

(57) ABSTRACT

A soft intraocular lens is provided, with IRHD hardness thereof being 40 to 60, wherein distance L is in a range of 3.75 mm-4.50 mm, which is a distance from an optical central axis of the optical part to a reference point of a supporting part side edge of the transition part, and an angle θ is in a range of 35°-50°, which is formed by a surface including the optical central axis and a reference point of the supporting part side edge of the transition part, and a surface including the optical central axis and in contact with a tip of the supporting part, with a width of the transition part being larger than a width of the supporting part, and a width Wm of the transition part in a middle of the optical part side edge and the supporting part side edge of the transition part being 1.5 times to 3 times of a width Ws of the supporting part.

8 Claims, 6 Drawing Sheets

SOFT INTRAOCULAR LENS

TECHNICAL FIELD

The present invention relates to a soft intraocular lens made of a single material, foldable, and having a structure suitable for being inserted into an eye by an injector.

DESCRIPTION OF RELATED ART

An increase of senile cataract patients has been conspicuous, with an increase of elderly population. A treatment of a cataract has been performed by methods such as removing a cloudy crystalline lens nucleus and cortex to thereby correct a poor vision by a spectacle lens or a contact lens, or inserting an intraocular lens into an eye. However, at present, a method of performing a total extirpation of a crystalline lens and thereafter fixing the intraocular lens to the eye, has been generally executed.

In recent years, with a spread of a phacoemulsification system, an intraocular lens that can be inserted from a small incision has been developed and is widely clinically used, for the purpose of reducing a postoperative astigmatism and a surgical invasion. This lens is a soft intraocular lens that can be inserted into an eye from a small incision, with its optical part folded, by using a soft material as an optical part material.

If soft intraocular lenses are roughly divided from a structural aspect, they are divided into a type in which an optical part and a supporting part are made of different kind of materials, and a type in which the optical part and the supporting part are made of the same material.

Generally, the intraocular lens of the type in which the optical part and the supporting part are made of different kind of materials, is constituted of an approximately circular optical part made of a foldable soft material such as silicon, acrylic resin, and hydrogel, and a supporting part with its end opened, and which is made of a hard material such as polypropylene and polymethylmethacrylate which are relatively harder than the aforementioned soft materials. Although such an intraocular lens is excellent in stability in the eye, it is said that a manufacturing cost is high due to complicated manufacturing steps, and a failure is possibly generated at a joint portion between the optical part and the supporting part.

In a case of the intraocular lens of the type in which the optical part and the support par are made of the same material, types of the supporting part include a disc type, a close loop type (see patent document 1), and an open loop type (see patent document 2), etc.
However, the present invention relates to a soft intraocular lens wherein the supporting part is the open loop type.

Meanwhile, various injectors have been developed, as instruments for inserting the intraocular lens from a further small incision of an eye. According to such injectors, a folded intraocular lens can be pushed out into an eye through a cylindrical insertion cylinder, and therefore the intraocular lens can be inserted into the eye from a tremendously small incision, compared with a case that the intraocular lens is inserted by using conventional tweezers.

Under such a circumstance, as functions and performances required for the intraocular lens in addition to an optical function of the intraocular lens, the following functions/performances can be given: (a) The intraocular lens can be held stable in an eye (in capsula lentis). (b) The intraocular lens can be folded smaller when passing through the injector and can pass therethrough smoothly.
Patent document 1: Published Japanese translation of a PCT application No. 1998-513099
Patent document 2: Published Japanese translation of a PCT application No. 2000-509615

DISCLOSURE OF THE INVENTION

Problem to be Solved by the Invention

However, in a conventional intraocular lens with an open loop type supporting part, the above-described functions are not sufficiently satisfied. For example, the intraocular lens described in patent document 1 has a problem that inconveniences are generated as described below. FIG. 6 is a view showing a state that an intraocular lens 200 of patent document 1 is inserted into an injector 300. As shown in FIG. 6, the intraocular lens 200 is folded into two and inserted from an insertion opening 301 of an injector 300. In this case, since a length of a supporting part 202 of the intraocular lens 200 of the patent document 1 is relatively long, thus involving a problem that the supporting part 202 located on the front side is twisted when the intraocular lens passes through an insertion cylinder of the injector 300, and can not be discharged into the eye. Further, although the supporting part 202 has a hinge structure, the supporting part lacks flexibility as a whole, thus involving a problem that a stress is concentrated locally in capsula lentis after insertion into the eye.

Further, the intraocular lens of the patent document 2 also has a problem due to the length of the supporting part as described above, and a problem that the intraocular lens is stuffed in the injector because the intraocular lens can not be folded small in the injector, due to an excessively large width near a root of the supporting part.

Further, in addition to the above-described problem, in a case of the intraocular lens having the open loop type supporting part, when the intraocular lens passes through the injector, there is a problem that the supporting part located on the rear side in the insertion cylinder is tangled in an injector plunger (pushing rod), or the supporting part located on the front side is sandwiched between the optical part and an inner wall of the insertion cylinder.

An object of the present invention is to solve the above-described problems, and provide the intraocular lens that can be held in the eye stably after being inserted into the eye, and the intraocular lens that can be folded small when the intraocular lens passes through the injector, and capable of passing there through smoothly.

Means for Solving the Problems

As means for solving the above-described problems, according to a first means, a soft intraocular lens is provided, which is a foldable intraocular lens, comprising:

an optical part;

a plurality of supporting parts provided on the outside of the optical part for holding the optical part in an eye; and a transition part provided between the optical part and the supporting part, wherein the optical part, the transition part, and the supporting part are integrally formed and made of the same material, with IRHD hardness thereof being 40 to 60, wherein distance L is in a range of 3.75 mm-4.50 mm, which is a distance from an optical central axis of the optical part to a reference point of a supporting part side edge of the transition part, and an angle θ is in a range of 35°-50°, which is formed by a surface including the optical central axis and a reference point of the supporting part side edge of the transition part, and a surface including the optical central axis and in contact with a tip of the supporting part, with a width of the transition part being larger than a width of the supporting part, and a width Wm of the transition part in a middle of an optical part side edge and the supporting part side edge of the transition part being 1.5 times to 3 times of a width Ws of the supporting part.

According to a second means, the soft intraocular lens according to the first means is provided, wherein the transition part is extended toward outside in approximately a radial direction.

According to a third means, the soft intraocular lens according to the first or second means is provided, wherein the width Ws of the supporting part is approximately fixed in a range of 0.3 mm-0.6 mm in an area between a surface including the optical central axis and the reference point, and a surface which is the surface including the optical central axis and which is formed by 20° with respect to the surface including the optical central axis and the reference point.

According to a fourth means, the soft intraocular lens according to any one of the first to third means is provided, wherein there are two supporting parts.

Advantage of the Invention

According to the first means, by setting L to 3.75 mm to 4.50 mm, and setting the angle θ to 35° to 50°, and simultaneously setting Wm to 1.5 times to 3 times of Ws, the intraocular lens can be folded small in the injector and can pass through the injector smoothly when passing there through without twisting or tangling the supporting part in the injector plunger or sandwiching the supporting part located on the front side between the optical part and the inner wall of the insertion cylinder, thus making it possible for the first time, to obtain the intraocular lens that can be held in an eye stably after being inserted into the eye.

Note that in a case that L is shorter than 3.75 mm, the supporting part needs to be set longer relatively. Therefore, there is a possibility that the front side supporting part is twisted in the injector insertion cylinder or the front side supporting part is sandwiched between the optical part and the inner wall of the cylinder, or a rear side supporting part is tangled in the plunger. Further, in a case that L is longer than 4.50 mm, the supporting part is relatively shorter, and a sufficient contact between the capsula lentis and the supporting part can not be obtained. Then, it can be considered that stability of the intraocular lens in the capsula lentis is deteriorated. In addition, there is also a possibility that centering in the capsula lentis is deteriorated.

When the angle θ is less than 35°, the sufficient contact between the capsula lentis and the supporting part can not be obtained, thus deteriorating the stability of the intraocular lens in the capsula lentis, or deteriorating the centering in the capsula lentis. When the angle θ exceeds 50°, the supporting part becomes longer accordingly, thus possibly twisting the front side supporting part in the injector insertion cylinder, or sandwiching the front side supporting part between the optical part and the inner wall of the cylinder, or tangling the rear side supporting part in the plunger.

When Wm is less than 1.5 times of Ws, strength of the transition part is weakened, thus possibly inducing a state that the front side supporting part is twisted in the injector insertion cylinder or the front side supporting part is sandwiched between the optical part and the inner wall of the cylinder. The intraocular lens is inhibited from passing through the injector insertion cylinder, in a case that Wm exceeds 3 times of Ws. The intraocular lens of a type having two supporting parts is particularly preferable, if a discharge from an injector with a small diameter is taken into consideration.

According to the second means, the transition part is extended approximately in a radial direction. Therefore, there is a less possibility that a peripheral part and the transition part of the intraocular lens is interfered with each other when being folded in the insertion cylinder, thus generating a scratch or failure in the transition part.

According to the third means, the width Ws of the supporting part is approximately fixed in a range of 0.3 mm-0.6 mm in an area between the surface including the optical central axis and the reference point, and a surface which is the surface including the optical central axis and which is formed by 20° with respect to the surface including the optical central axis and the reference point. Therefore, almost uniform suitable flexibility can be provided over an entire body of the supporting part, thus making it possible to suppress a pressure small, which is locally applied to the capsula lentis from the supporting part. Note that here, the reference point means a midpoint on a boundary line between the transition part and the supporting part, and the boundary line between the transition part and the supporting part means a straight line showing a width at a part where the width of the transition part is minimum so as to be equal to the width of the supporting part.

In a case that Ws is smaller than 0.3 mm, a repulsive force from the capsula lentis to the supporting part is weak, thus deteriorating the stability in the eye or deteriorating the centering, and in a case that Ws is larger than 0.6 mm, the flexibility can not be obtained, and the pressure locally applied to the capsula lentis form the supporting part is excessively large. Further, in a case that the aforementioned angle is 20° or less, there is a possibility that the flexibility as an entire body of the supporting part is deteriorated.

BEST MODE FOR CARRYING OUT THE INVENTION

FIG. 1 is a planar view of a soft intraocular lens according to an embodiment of the present invention, FIG. 2 is a cross-sectional view of FIG. 1 taken along the line I-I, FIG. 3 is a partially expanded view of FIG. 1, FIG. 4 is a view showing an intermediate body in a middle of a manufacture of the soft intraocular lens according to the present invention, wherein FIG. 4A is a planar view and FIG. 4B is a cross-sectional view taken along the line A-A. The soft intraocular lens according to preferred embodiments of the present invention will be described hereafter, with reference to these figures.

As shown in FIG. 1, the soft intraocular lens according to an embodiment has an optical part 1; two supporting parts 2 provided at almost symmetrical positions with a central axis O of the optical part 1 as a center; and a transition part provided between the optical part 1 and the supporting part 2. In this intraocular lens, the optical part 1, the support par 2, and the transition part 3 are made of the same soft material and are integrally formed, and therefore this intraocular lens is a so-called one piece type soft intraocular lens.

The optical part 1 is formed of a convex lens with almost a circular shape having radius r1 in a planar view. The transition part 3 is risen outward from a root of a large width, namely, from a side edge of the optical part of the transition part, in an outer peripheral part of the optical part 1, in such a manner as being narrower in width, and at a position where the width is the same as the width (Ws) of the supporting part 2, namely, at the side edge of the supporting part of the transition part, transition to the supporting part 2 occurs. The supporting part 2 is provided in such a manner as being folded toward the optical part 1 from the vicinity of the side edge of the supporting part of the transition part 3, and extended by a specified distance with a fixed width (Ws) and thickness (Ts). Note that the width Ws of the supporting part 2 is preferably set to the thickness Ts or less of the supporting part 2. Thus, a possibility of twisting the supporting part 2 can be reduced. Note that the thickness of the transition part 3 is Tm which is thinnest at an end portion close to the optical part 1 of the transition part 3, and is almost the same thickness Ts as the thickness of the supporting part 2 at an end portion close to the supporting part 2 of the transition part 3. In a case of a refractive index 20 diopter, Tm=0.2 mm and Ts=0.4 mm.

Next, structures of the supporting part 2 and the transition part 3 are described in detail, with reference to FIG. 3. Here, two points P1 and P2 are set, which are the points where a curve that partitions a profile of the transition part 3 in a planar view is separated from a circle having radius r1 which draws the profile of the optical part 1 in the planar view at the root of the transition part 3. Then, the rise of the two profiles is observed, which partition both widths of the transition part 3 in an appearance of drawing a curve outward, with points P1 and P2 as base points.

The curved with point P1 as a base point is the curve with curvature radius R1, and point P3 is set as an end point of this curve. Note that the center of the curvature of this curve is located outside of the optical part. Meanwhile, the curve with point P2 as a base point is the curve with curvature radius R2, and point P4 is set as an end point of this curve. This curve has an appearance of a convex shape toward the curve with point P1 as a base point. Next, a straight line portion with point P5 as an end point thereof is formed as a tangent line in contact with the curve with curvature radius R1 at point P3 with this point P3 set as a start point. In this embodiment, R1=0.75 mm, R2=2.25 mm.

Further, there is formed a curve with curvature radius R3 with point P4 as a start point, being a curve that rises in a direction of a tangent line in contact with the curve with curvature radius R2 at this point P4, with a convex direction set to be opposite to a convex direction of the curve with curvature radius R2, with point P5 as its end point. Further, there is formed a curve with curvature radius R4 with the point P5 as a start point, being a curve that rises in a straight line direction of the straight line portion at this point P5, with a convex direction set to be the same as a convex direction of the curve with curvature radius R1, with point P7 as its end point. In this embodiment, R3=0.7 mm, R4=0.3 mm.

Further, there is formed a curve with curvature radius R5 with point P6 as a start point, being a curve that rises in a direction of a tangent line in contact with the curve with curvature radius R3 at this point P6, with a convex direction set to be the same as a convex direction of the curve with curvature radius R3, with point P8 as its end point. Further, there is formed a curve with curvature radius R6 with point P7 as a start point, being a curve that rises in a direction of a tangent line in contact with the curve with curvature radius R4 at this point P7, with a convex direction set to be the same as a convex direction of the curve with curvature radius R4, with point P9 as its end point. Then, a smooth convex curve is formed outward between point P8 and point P9. In this embodiment, R5=4.75 mm, R6=4.35 mm.

Here, a distance between point P1 and point P2 of the transition part 3 is w1, and a width in an intermediate part of the transition part 3 is Wm, and a width of the supporting part 2 is Ws. In this embodiment, Wm=0.63 mm, Ws=0.4 mm. In addition, Ws is preferably 0.3 mm to 0.6 mm.

Further, Wm is preferably 1.5 times to 3 times of the width Ws of the supporting part. In a case that Wm is less than 1.5 times of Ws, the strength of the transition part is weakened, thus possibly inducing a problem that the front side supporting part is twisted in the injector insertion cylinder, or the front side supporting part is sandwiched between the optical part and the inner wall of the cylinder. The intraocular lens is inhibited from passing through the injector insertion cylinder, in a case that Wm exceeds 3 times of Ws.

Further, width Wm in the intermediate part of the transition part 3 is defined as follows. Namely, first, the optical part side edge of the supporting part 2, in other words, the supporting part side edge of the transition part 3 is located at a part where the width of the transition part 3 is Ws. This means that K3 is defined as a point where a straight line that connects the point P4 and the point O4, and the curve with curvature radius R4 are intersected with each other, the point O4 being a curvature center between curvature radius R3 and curvature radius R4, and at this time, straight line P4K3 is located at a supporting part side edge of the transition part 3 or at a transition part side edge of the supporting part 2.

A midpoint of this straight line P4K3 is defined as K, and the point K is set as a reference point of the supporting part side edge of the transition part 3. Then, regarding a circle with central axis O of the optical part 1 as a center, a radius of this circle passing through the point K is defined as r3. Then, a circle with radius r2 satisfying r2=(r1+r3)/2, with the central axis O of the optical part 1 as a center, can be assumed. Then, points where this circle and a profile line of the transition part 3 are intersected, are defined as K1 and K2. At this time, length Wm of a straight line K1K2 corresponds to a width in a middle of the transition part 3. In this embodiment, r1=3.00 mm, r3=4.06 mm, r2=3.53 mm, Wm=0.63 mm.

Further, an angle θ is defined to be formed by surface S1 including the central axis O (optical axis) of the optical part and the point K, and surface S2 which is the surface including the optical axis in contact with point P9 of a tip of the supporting part 2. In this embodiment, θ=44.9°. Note that θs≤θ≤θm is preferable. Here, θs=35.0°, and θm=50°. In a case that θ is less than 35°, a sufficient contact between the capsula lentis and the supporting part can not be obtained, thus deteriorating the stability of the intraocular lens in the capsula lentis, or deteriorating the centering in the capsula lentis. When θ exceeds 50°, there is a possibility that the front side supporting part is twisted in the injector insertion cylinder, or the supporting part is sandwiched between the optical part and the inner wall of the cylinder, or the rear side supporting part is tangled in the plunger.

Further, the point P8, being an outer peripheral end of the supporting part 2, is located on a circle having radius r4 with the central axis O (optical axis) of the optical part 1 as a center. In this embodiment, r4=6.25 mm. Further, when a distance between the central axis O of the optical part 1 and a reference point K of the supporting part side edge of the transition part 2 is defined as L, this distance L is equal to the radius r3, and in this embodiment, L=r3=4.50 mm. Here, 3.75 mm≤L≤4.25 mm is preferable.

In a case that L is shorter than 3.75 mm, the supporting part needs to be relatively longer. Therefore, there is a possibility that the front side supporting part is twisted in the injector insertion cylinder, or the supporting part is sandwiched between the optical part and the inner wall of the cylinder, or the rear side supporting part is tangled in the plunger. Further, in a case that L is longer than 4.50 mm, the supporting part is relatively shorter, and a sufficient contact between the capsula lentis and the supporting part can not be obtained, thus deteriorating the stability of the intraocular lens in the capsula lentis or deteriorating the centering in the capsula lentis.

FIG. 5 is a view showing a state that the intraocular lens 100 according to the embodiment of the present invention is inserted into the injector 300. As shown in FIG. 5, the intraocular lens 100 is folded into two, and is inserted into the injector 300 from the insertion opening 301. In this case, since the length of the supporting part 2 of the intraocular lens 100 of this embodiment has a suitable length and a suitable flexibility, etc., the intraocular lens can pass through the insertion cylinder of the injector 300 smoothly without twisting the supporting part 2 located on the front side when passing through the insertion cylinder, and can be discharged into the eye excellently.

The soft intraocular lens with this structure is manufactured as described below. Namely, surface formation machining for forming a curved surface, being the optical surface 1, the supporting part 2, and the transition part 3, is applied to front and rear surfaces of a raw material 10 whose planar view is shown in FIG. 4A, by using a precisive lathe machine. FIG. 4B is a cross-sectional view of the raw material 10 after processing, taken along the line A-A. As shown in the figure, the optical part 1 is formed on the curved surface that forms a lens, and a concentric portion that forms the supporting part 2 is formed into a flat surface, and a portion that forms the transition part 3 is formed into a curved surface whose thickness is changed in a radius direction. Note that the above-described all steps can be performed by cast-molding, or the steps up to the surface formation machining can be performed by cast-molding. A disc-shaped raw material 10 thus machined is cut-out into a shape of the intraocular lens shown by dot line in FIG. 3A by using a milling device, etc. Thus, the soft intraocular lens is obtained. Further, in order to improve visibility, or prevent the supporting part and the optical part from sticking to each other, the surface of the supporting part, or the surface of the supporting part and the surface of the transition part can be machined like a frosted glass. Note that as a soft material that forms the raw material 10, soft acryl, hydrogel, or silicone, etc., can be used.

FIG. 7 is a partially expanded planar view of the soft intraocular lens according to other embodiment of the present invention. The soft intraocular lens according to other embodiment of the present invention will be described, with reference to FIG. 7. As shown in FIG. 7, the soft intraocular lens according to this embodiment is a one-piece type soft intraocular lens, which also has the optical part 1, two supporting parts 2, and the transition part 3, and they are integrally formed by the same soft material, and an essential structure is the same as the structure of the aforementioned embodiment, and therefore mainly a different point is explained and an explanation for the same point is omitted.

Different points of this embodiment from the aforementioned embodiment are values of r2 and r3, and specific shapes and dimensions of the supporting part 2 and the transition part 3. In this embodiment, r2=3.50 mm and r3=4.00 mm. Further, in the transition part 3, curvature radius R1 of the curve with point p1 as a base point and point 3 as an end point is expressed by R1=0.86 mm, and curvature radius R2 of the curve with point P2 as a base point and point P4 as an end point is expressed by R2=0.75 mm.

Curvature radius R4 of the curve with point P3 as a start point and point P5 as an end point is expressed by R4=0.40 mm, and curvature radius R3 of the curve with point P4 as a start point and point P6 as an end point is expressed by R3=0.75 mm. Here, an end point of the curve with point P5 as a start point is point P10, and its curvature radius is R5=4.5 mm. Also, an end point of the curve with point P5 as a start point is point P9, and its curvature radius is R6=4.10 mm.

Then, a curve with curvature radius R7 with point P11 as an end point is formed, which is a curve with point P9 as a start point, rising in a tangent line direction in contact with the curve with curvature radius R6 at this point P9, with the same convex direction as the convex direction of the curve with curvature radius R6. In this embodiment, R7=1.50 mm. Also, a curve with curvature radius R8 with point P12 as an end point is formed, which is a curve with point P11 as a start point, rising in a tangent line direction in contact with the curve with curvature radius R7 at this point P11, with opposite convex direction to the convex direction of the curve with curvature radius R7. In this embodiment, R8=0.40 mm. The point 12 is a tip of the supporting part 2 in contact with a surface including the optical axis O. Angle θ is expressed by θ=4.60°, which is an angle formed by a surface including the central axis O and passing through the aforementioned point P12, and a surface including the central axis O (optical axis) and passing through the reference point K. A portion with point P12 as a start point and point P13 as an end point on a surface including the optical axis O is a straight line portion, and a curve between the point P13 and the point P10 is a smooth curve with convex shape outward.

The transition part 3 is located in an area between curve P1P2 that partitions a root, and straight line K3K4 that partitions a boundary between the transition part 3 and the supporting part 2. Regarding a width of the intermediate part of this transition part 3, length Wm of the straight line K1K2 is expressed by Wm=0.66 mm when points are defined as K1 and K2 where the circle with radius r2 and right and left profile lines of the transition part are crossed with each other, and this length Wm is the width of the intermediate part. The reference point K is a point on the circle with radius r3, being a midpoint of the straight line K1K2. Straight line K3K4 that partitions the boundary between the transition part 3 and the supporting part 2 is a straight line showing a width of a part where the width of the transition part 3 is narrowest, being the width Ws which is close to the optical part 1 of the supporting part 2. An area of the width Ws extends to an area that connects points P8 and P9, and the width is gradually larger there from toward the tip, leading to a maximum width Wn=0.80 mm at a part close to the tip of the supporting part 2. In this case, angle θn is expressed by θn=25.9° which is an angle formed by a surface including the central axis O and passing through midpoint K5 of straight line P8P9, and a surface including the central axis O (optical axis) and passing through the reference point K.

According to this embodiment, by particularly expanding the tip side of the supporting part, the intraocular lens can be stably held in the eye after being inserted into the eye, and a possibility of tangling of the supporting part can be reduced, thus allowing a smooth passage of the lens.

INDUSTRIAL APPLICABILITY

The present invention can be utilized as an intraocular lens which is inserted into an eye and fixed thereto after a total extirpation of a crystalline lens.

BRIEF DESCRIPTION OF THE DRAWINGS

FIG. 4 is a view showing an intermediate body in a middle of a manufacture of the soft intraocular lens according to the present invention, wherein FIG. 4A is a planar view and FIG. 4B is a cross-sectional view taken along the line A-A.

DESCRIPTION OF SIGNS AND NUMERAL

Figure 1:
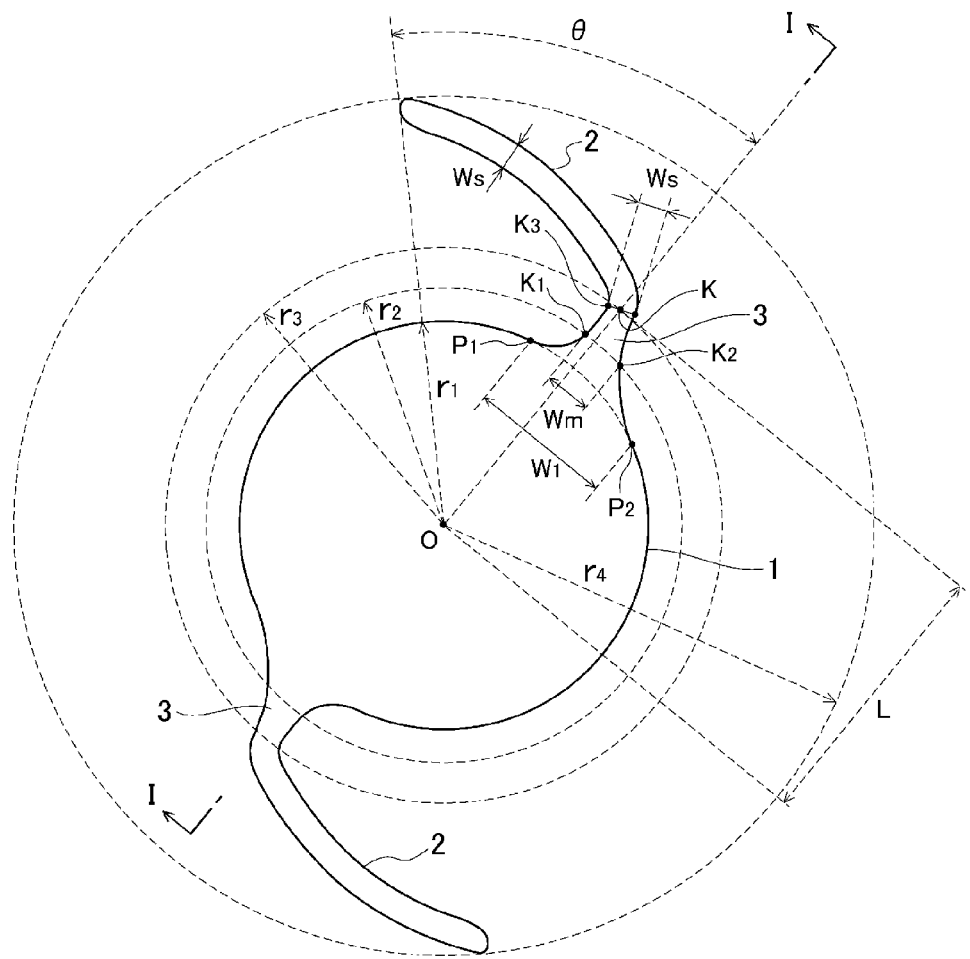
FIG. 1 is a planar view of a soft intraocular lens according to an embodiment of the present invention.
Figure 2:
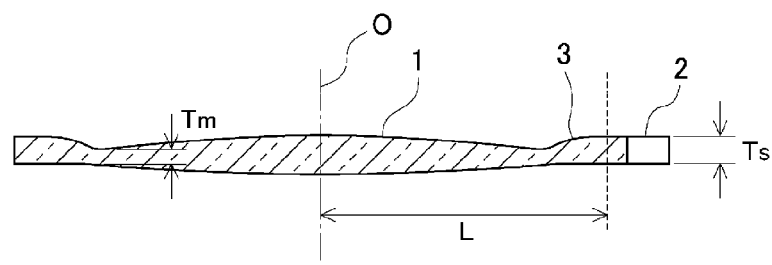
FIG. 2 is a cross-sectional view of FIG. 1 taken along the line I-I.
Figure 3:
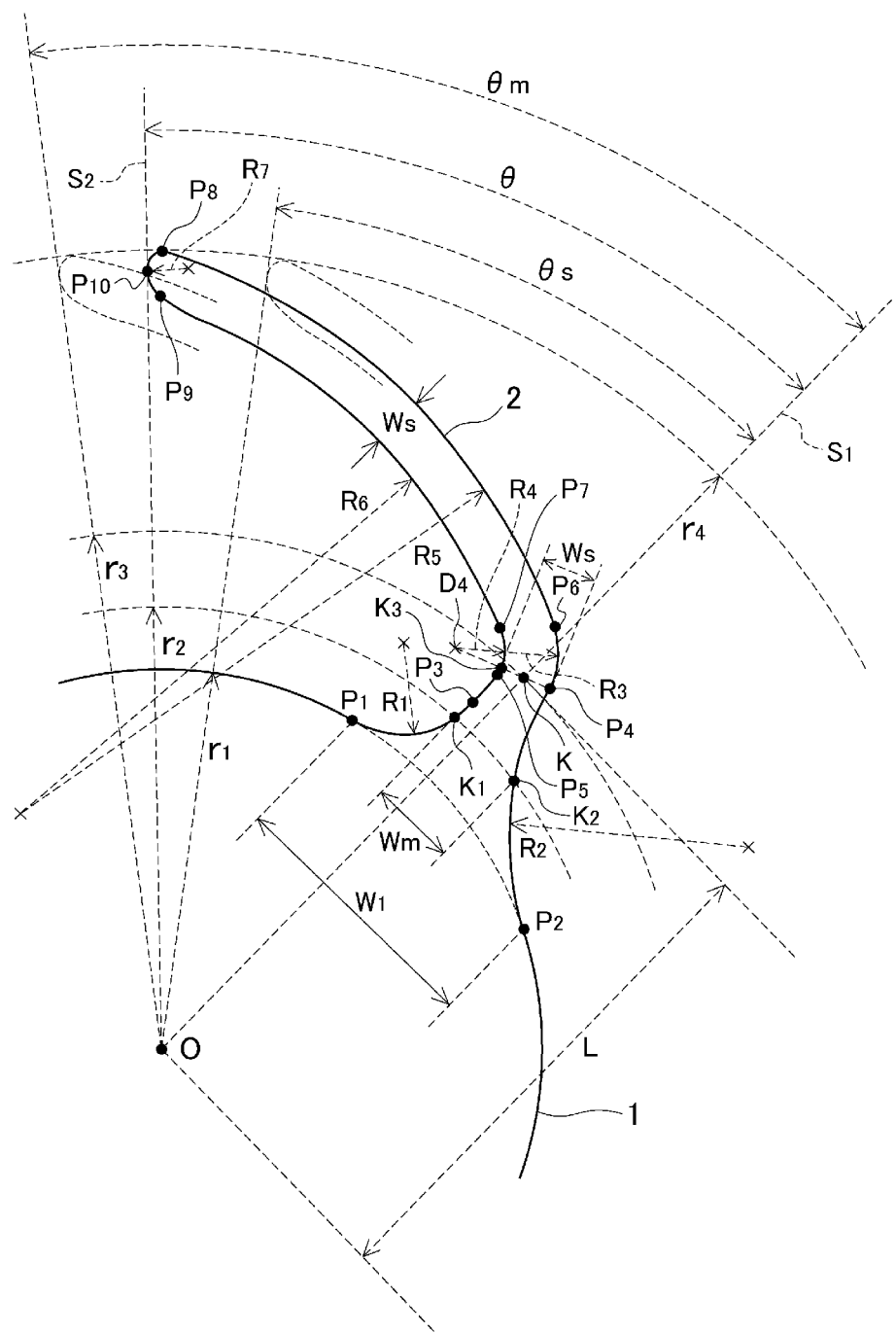
FIG. 3 is a partially expanded view of FIG. 1.
Figure 4:
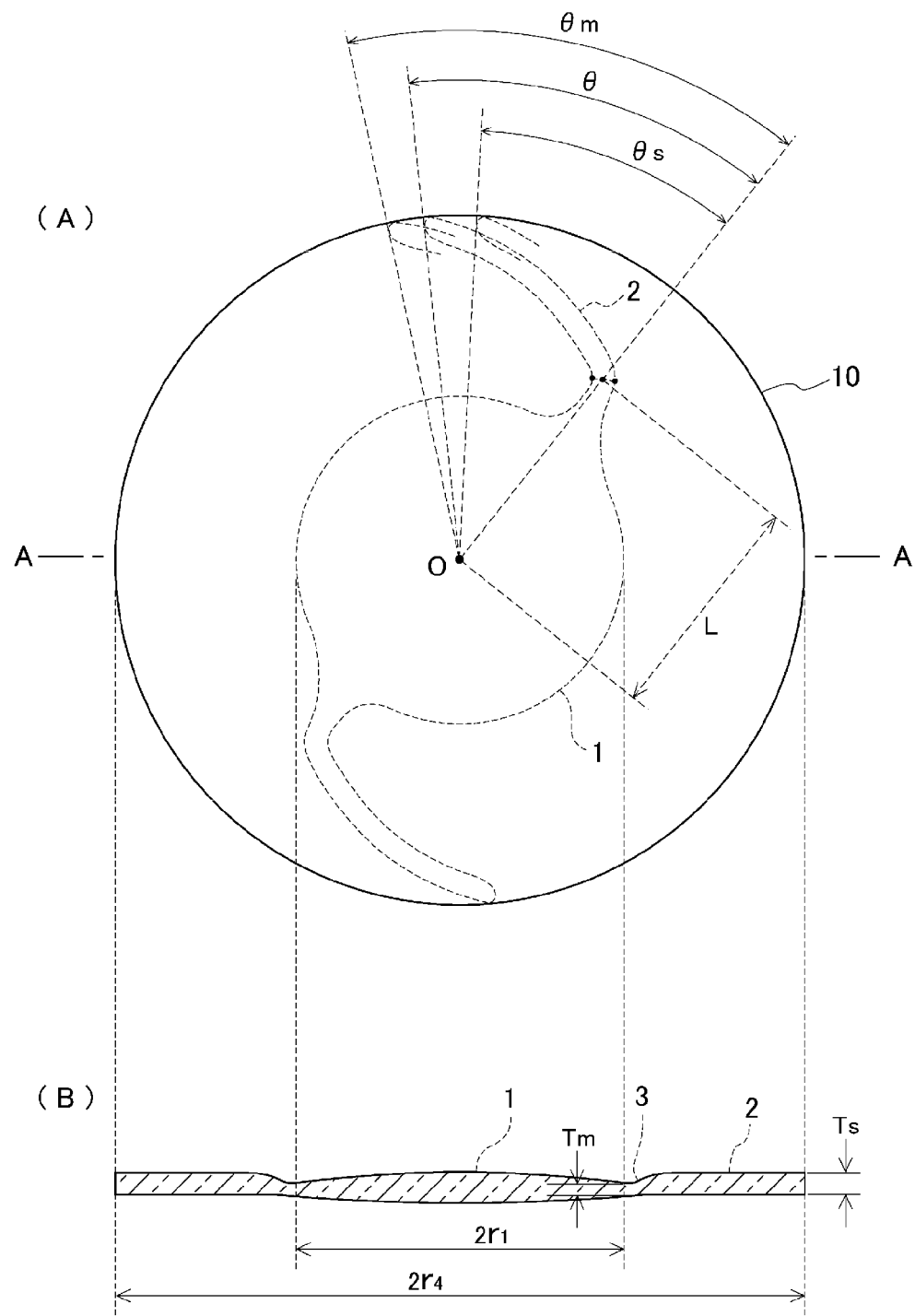
Figure 5:
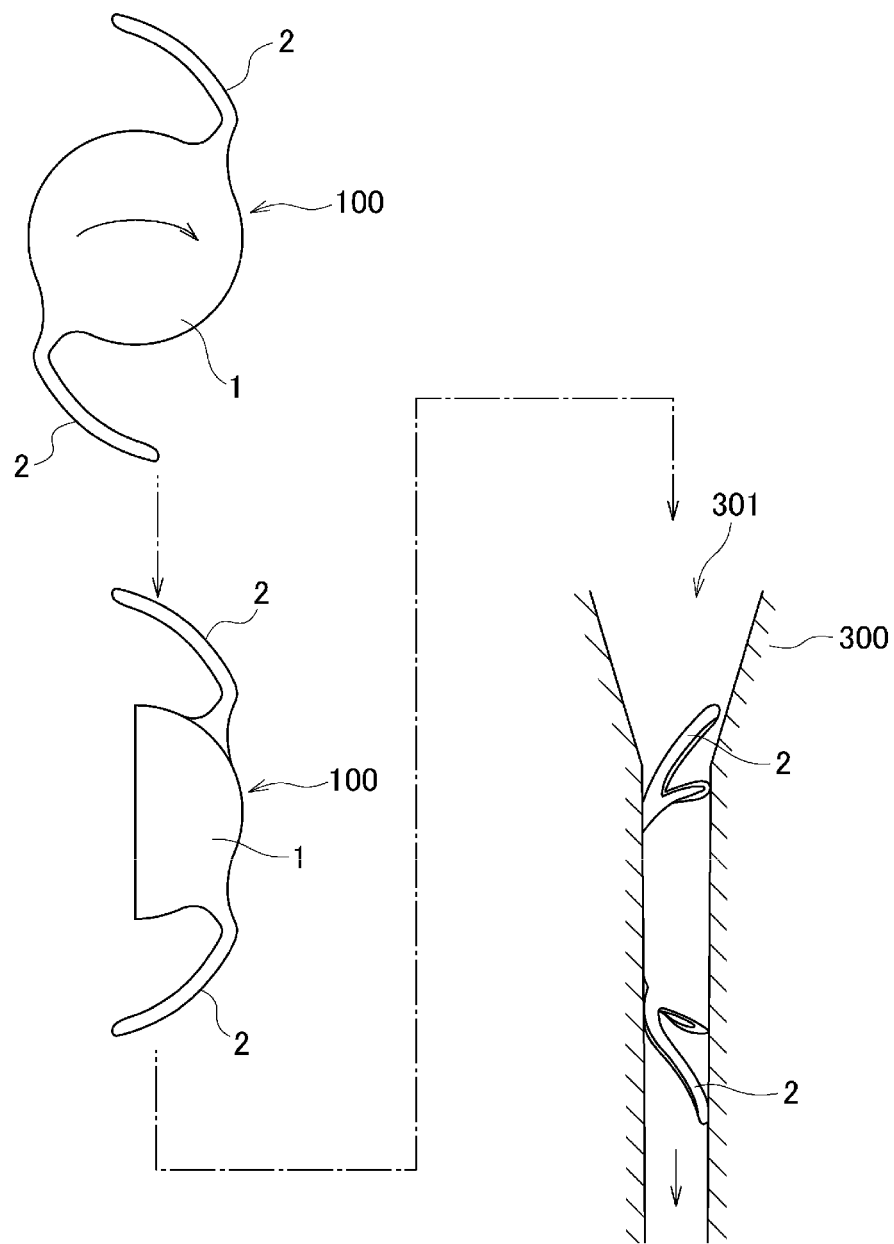
FIG. 5 is a view showing a state that an intraocular lens 100 according to an embodiment of the present invention is inserted into an injector 300.
Figure 6:
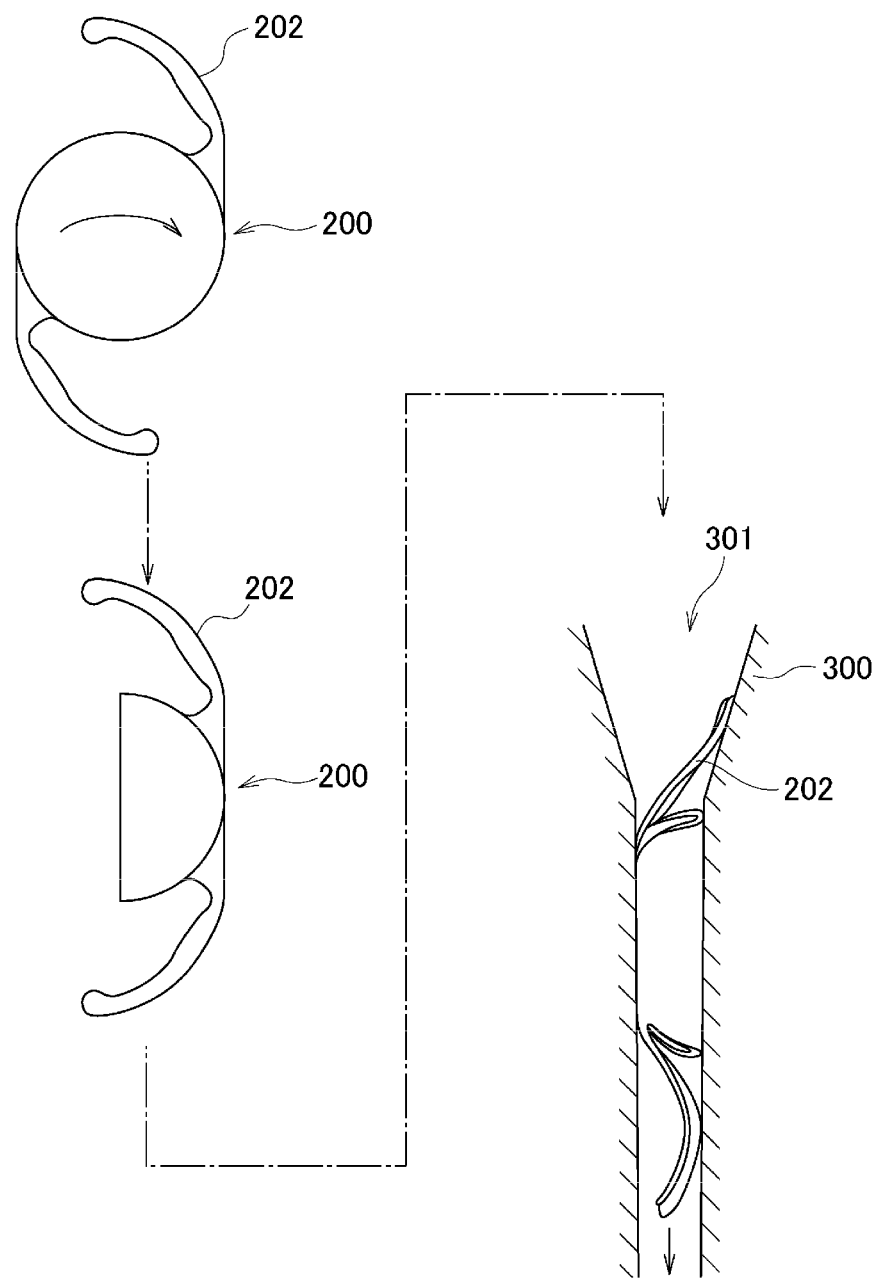
FIG. 6 is a view showing a state that an intraocular lens 200 of patent document 1 is inserted into the injector 300.
Figure 7:
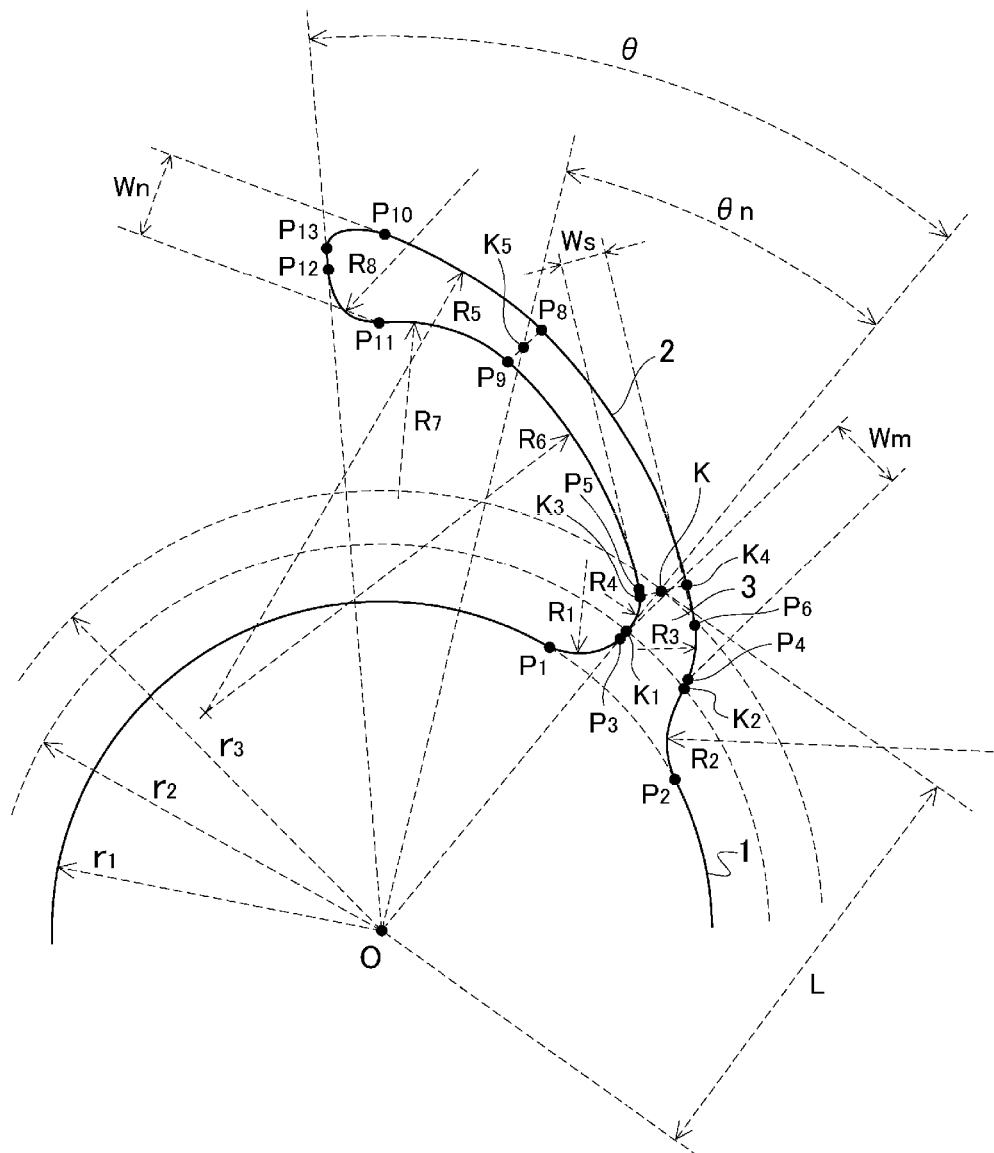
FIG. 7 is a partially expanded view of the soft intraocular lens according to other embodiment of the present invention.

1 Optical part
2 Supporting part
3 Transition part

The invention claimed is:

1. A soft foldable intraocular lens, comprising:
an optical part defining a central axis O that extends in an anterior-posterior direction and an optical part outer boundary;
first and second supporting parts for holding the optical part in an eye, each supporting part defining a width Ws over at least a portion thereof and having a support part tip and a support part root; and
first and second transition parts, each transition part defining a respective radially inner boundary that is coincident with a respective portion of the optical part outer boundary and each transition part defining a respective radially outer boundary that is radially spaced from that transition part's radially inner boundary and is coincident with a respective one of the first and second supporting part roots, the radially outer boundary of each transition part defining a mid-point, and each transition part defining a width that continuously increases from the width Ws at the radially outer boundary to a width W1 at the radially inner boundary and also defining a width Wm at the radial mid-point between the radially inner boundary and the radially outer boundary;
wherein the width Ws, width W1 and width Wm extend in respective directions that are perpendicular to the anterior-posterior direction;
wherein the optical part, the first and second transition parts, and the first and second supporting parts are integrally formed and made of the same material, with IRHD hardness thereof being 40 to 60;
wherein for at least the first supporting part and the first transition part
a reference point K is located at the mid-point of the radially outer boundary of the transition part,
a distance L, measured along a straight line, from the optical part central axis O to the reference point K is 3.75 mm-4.50 mm,
an angular offset θ about the central axis O from the tip of the supporting part to the reference point K is 35°-50°, and
the transition part radial mid-point width Wm is 1.5 times to 3 times the supporting part width Ws.

2. The soft intraocular lens according to claim 1, wherein the first and second transition parts extend outwardly in a generally radial direction.

3. The soft intraocular lens according to claim 1, wherein the supporting part width Ws is approximately 0.3 mm-0.6 mm in an area that extends from the reference point K to a point that is angularly offset from the reference point K by 20°.

4. The soft intraocular lens according to claim 1, wherein for the second supporting part and the second transition part
a reference point K is located at the mid-point of the radially outer boundary of the transition part,
a distance L from the optical part central axis O to the reference point K is 3.75 mm-4.50 mm,
an angular offset θ about the central axis O from the tip of the supporting part to the reference point K is 35°-50°, and
the transition part radial mid-point width Wm is 1.5 times to 3 times the supporting part width Ws.

5. The soft intraocular lens according to claim 2, wherein the supporting part width Ws is approximately 0.3 mm-0.6 mm in an area that extends from the reference point K to a point that is angularly offset from the reference point K by 20°.

6. The soft intraocular lens according to claim 1, wherein the supporting part width Ws is constant over the majority of the supporting part.

7. The soft intraocular lens according to claim 1, wherein the supporting part width Ws is constant in a region adjacent to the radially outer boundary of the transition part.

8. The soft intraocular lens according to claim 1, wherein the supporting part width Ws is no greater than the width at the radially outer boundary of the transition part in the region adjacent to the radially outer boundary of the transition part.

* * * * *